United States Patent [19]
Gumbrecht et al.

[11] Patent Number: 5,763,760
[45] Date of Patent: Jun. 9, 1998

[54] METHOD FOR CALIBRATION OF GAS MEASURING SENSORS FOR DISSOLVED GASSES AND METHOD FOR MEASURING THE CONCENTRATION OF $CO_2$ IN BLOOD WITH THE ASSISTANCE OF SUCH A CALIBRATION METHOD

[75] Inventors: Walter Gumbrecht, Herzogenaurach; Manfred Stanzel, Bubenreuth, both of Germany

[73] Assignee: Siemens Aktiengesellschaft, Munich, Germany

[21] Appl. No.: 799,532

[22] Filed: Feb. 13, 1997

[30] Foreign Application Priority Data

Feb. 13, 1996 [DE] Germany ............... 196 05 246.7

[51] Int. Cl.[6] .................................................. G01N 33/00
[52] U.S. Cl. ...................................................... 73/1.06
[58] Field of Search .................... 73/19.1, 1.02–1.07; 436/8, 9, 11; 422/98

[56] References Cited

U.S. PATENT DOCUMENTS

| | | | |
|---|---|---|---|
| 4,905,497 | 3/1990 | Shindo et al. | 73/1.03 |
| 5,185,263 | 2/1993 | Kroneis et al. | 73/1.02 |
| 5,207,087 | 5/1993 | Costello | 73/1.06 |
| 5,212,092 | 5/1993 | Jackson et al. | 73/1.02 |
| 5,234,835 | 8/1993 | Nestor et al. | 436/8 |
| 5,329,804 | 7/1994 | Germany | 73/1.06 |

*Primary Examiner*—Robert Raevis
*Attorney, Agent, or Firm*—Hill & Simpson

[57] ABSTRACT

Method for calibrating gas measuring sensors for dissolved gasses and method for measuring the concentration of $CO_2$ in blood with the assistance of such a calibration method two or more separate calibration fluids in which a gas to be measured is dissolved with respectively different partial pressures are employed. For simplification, another (i.e., a second) calibration fluid is produced from one (i.e., a first) calibration fluid by modifying the partial pressure of the first calibration fluid to a different value, preferably by material transport between the first fluid and a gas phase. Analysis equipment operating with this method, particularly for $CO_2$ measurement of blood, become simpler, smaller and less expensive.

23 Claims, 3 Drawing Sheets

METHOD FOR CALIBRATION OF GAS MEASURING SENSORS FOR DISSOLVED GASSES AND METHOD FOR MEASURING THE CONCENTRATION OF CO₂ IN BLOOD WITH THE ASSISTANCE OF SUCH A CALIBRATION METHOD

BACKGROUND OF THE INVENTION

1. Field of the Invention

The present invention is directed to a method for calibrating a sensor for measuring the concentration of a gas dissolved in a liquid and to a method for measuring the concentration of $CO_2$ dissolved in blood with the assistance of such a calibration method.

2. Description of the Prior Art

Examples of sensors for measuring the concentration of a gas dissolved in a liquid are chemical sensors for measuring the concentration of blood gases, particularly $CO_2$, $O_2$ and/or $N_2$ dissolved in blood.

In the case of sensors for measuring the concentration of a gas dissolved in a liquid, a distinction can be made, among other things, between, for example, (a) sensors that generate a measured value proportional to a logarithm of the concentration of the gas dissolved in the liquid, and (b) sensors that generate a measured value directly proportional to the concentration of the gas dissolved in the liquid.

An example of a sensor of type (a) is a potentiometric chemical sensor for measuring the concentration of $CO_2$ dissolved in blood that generates a measured value corresponding to the $CO_2$ concentration in the form of an electrical voltage that is proportional to the logarithm of the measured $CO_2$ concentration.

An example of a sensor type (b) is an amperometric chemical sensor for measuring the concentration of $O_2$ in blood that generates a measured value corresponding to the measured $O_2$ concentration in the form of an electrical current whose intensity is directly proportional to the measured $O_2$ concentration.

As is known, one basis for identifying the concentration of a gas dissolved in a liquid is to measure the partial pressure of the gas dissolved in this liquid, and it is standard, at least in medicine, to indicate the concentration of a dissolved gas by means of this pressure. With reference to gases dissolved in liquids or contained in gas phases, the terms "concentration" and "partial pressure" are synonymously employed wherever it is not critical to make a distinction. When a distinction is to be made, this is pointed out.

In order to be able to allocate the correct concentrations or partial pressures to the measured values supplied by the sensors, they must be calibrated and, if necessary recalibrated from time to time. For calibration, at least two calibration fluids respectively containing the gas dissolved in an exactly defined different concentrations are supplied to the sensor and measured values corresponding to these different concentrations or partial pressures are acquired.

The production of the calibration fluids with respectively different, exactly defined concentrations of the dissolved gas usually ensues such that the calibration fluids are produced separately from one another and separately supplied to the sensor for concentration measurement.

Various manufacturers of clinical analysis equipment (for example, the companies Ciba-Corning, Instrumentation Laboratory, NOVA, Radiometer or AVL) make use of various methods for producing the calibration fluids in apparatus for measuring the concentration of blood gases:

The mixtures are taken from two compressed gas cylinders that contain defined gas mixtures that differ from one another and are composed, for example, of $CO_2$, $O_2$ and/or $N_2$ and a saturated flow of the mixture is conducted over the sensor, whereby the calibration fluids are established by the saturated gas mixtures.

Various, defined gas mixtures are taken with a built-in gas mixing apparatus from two compressed gas cylinders that, for example, contain synthetic air and $CO_2$ and are conducted over the appertaining sensor in a saturated flow, whereby the calibration fluids are established by the saturated gas mixtures.

$CO_2$ is taken from a compressed gas bottle and is mixed with ambient air in a gas mixing apparatus, so that various gas mixtures with $CO_2$ concentrations that differ from one another are available, various calibration fluids being capable of being produced therefrom by introducing a respective gas stream into a respective pH buffer solution with a defined pressure.

Two manufacturers of intra-arterial blood gas monitoring systems (Puritan Bennet, Paratrend 7) employ a method wherein various gas mixtures are taken from two to three compressed gas cylinders and are conducted through calibration cells for the one-time calibration of these systems before they are placed in operation.

The Mallinkrot company pursues a different course that entirely omits compressed gas bottles and offers two tonometrified (appropriately pressurized) calibration fluids in metal-coated, gas-impermeable plastic bags for specific analysis apparatus of this company.

SUMMARY OF THE INVENTION

An object of the present invention is to provide a calibration method of the type initially described that can be more simply implemented compared to known calibration methods of this type.

The above object is achieved in accordance with the principles of the present invention in a method for calibrating a sensor for measuring a concentration of a gas dissolved in a fluid and for generating a measured value corresponding to the measured concentration, wherein a predetermined calibration fluid is conventionally produced which has a known, first concentration of the gas in question dissolved therein, and at least one further calibration fluid is produced from the predetermined calibration fluid by modifying the gas concentration present in the predetermined calibration fluid to a predetermined, other concentration in the further calibration fluid. Both the predetermined calibration fluid and the at least one further calibration fluid are then supplied to the sensor to be calibrated, and appropriate measured values are obtained respectively corresponding to the different gas concentrations in the two calibration fluids.

A particular advantage of the inventive method is that only one calibration fluid, the predetermined fluid need be produced in a conventional way. This advantageously allows the analysis apparatus using such a calibration method to be made simpler, smaller and less expensive.

Preferably and advantageously, the change of the concentration of the gas dissolved in the predetermined calibration fluid to the predetermined, other concentration is produced by a transport of material between the predetermined calibration fluid and a predetermined gas phase.

The gas phase to be employed can be freely selected within broad limits and is only subject to the limitation that the material transport, for example a gas exchange, between the predetermined calibration fluid and this gas phase must produce a change in the concentration of the gas dissolved in this calibration fluid.

Preferably the partial pressure of the gas in the calibration fluid is raised by material transport between the gas phase and the calibration fluid in that case wherein the partial pressure of the gas is higher in the gas phase than in the predetermined calibration fluid, and the partial pressure of the gas in the calibration fluid is lowered by material transport between the gas phase and the calibration fluid in that case wherein the partial pressure of the gas in the gas phase is lower than in the predetermined calibration fluid.

This is a case where a distinction must be made between partial pressure and concentration since the concentration and the partial pressure are related with a different proportionality factor in a gas dissolved in a liquid in comparison to a gas contained in a gas phase. The material transport between liquid and gas phase on the basis of a difference in partial pressure fails when the partial pressures of the gas in the gas phase and in the liquid have approached one another. Due to the different proportionality factors of gas phase and liquid, however, the concentration of the gas in the gas phase is different from that in the liquid in this condition. A distinction need not be made between concentration and partial pressure, however, wherever the proportionality factors are the same as or comparable to one another, so that they need not be discriminated, for example given a gas dissolved in two similar liquids or contained in two similar gas phases. In the discussion of this latter instance below, p stands both for partial pressure and for concentration. The concentration of non-volatile substances dissolved in liquid is referenced c.

The gas phase can be a gas mixture in which the gas dissolved in the predetermined calibration fluid is not contained, or in which it is contained with a proportionally higher or lower partial pressure than in the predetermined calibration fluid.

Preferably, a gas phase composed of air is employed, this advantageously being the ambient air in which the analysis apparatus being calibrated is disposed because special measures or containers for offering the gas phase are then not necessary. The necessity for such special measures or containers in known systems makes the apparatus more complicated and more expensive.

A gas phase can also be employed that is composed only of the gas dissolved in the predetermined calibration fluid, whereby, dependent on the pressure difference between the gas forming the gas phase and the partial pressure of this gas dissolved in the predetermined calibration fluid, the partial pressure or the concentration of the gas in this calibration fluid is also raised or lowered.

Gas phases can also be employed wherein the concentration or the partial pressure of the gas dissolved in the calibration fluid is modified by material transport on the basis of a different working mechanism than partial pressure compensation by itself. For example, a chemical reaction can be initiated in the predetermined calibration fluid on the basis of the material transport or gas exchange. This chemical reaction causes the gas dissolved in this liquid to partially disappear and thereby lowers the concentration or the partial pressure of this gas in this calibration fluid, or allows this gas to additionally arise and thereby increases the concentration or the partial pressure of this gas in this calibration fluid.

In an embodiment of the invention, the predetermined calibration fluid is supplied to the sensor through a tube having a gas-permeable tube wall surrounded by the aforementioned gas phase, and having an interior cross-section dimensioned so as to be small relative to the quantity of predetermined calibration fluid to be delivered to the sensor per unit of time. This dimensioning means that the predetermined calibration fluid in the tube will experience substantially no modification of the concentration of the gas dissolved therein, beyond a prescribable, permissible degree due to a material transport between this fluid and the gas phase through the tube wall during delivery of the predetermined calibration fluid to the sensor. The further calibration fluid, having the predetermined, other concentration of the gas in question can then be produced from the aforementioned predetermined calibration fluid by allowing the predetermined calibration fluid to dwell temporarily in the tube, thereby allowing a limited amount of material transport between the predetermined calibration fluid in the tube and the exterior gas phase via the gas-permeable tube wall.

Thus in this embodiment, the calibration fluids can be supplied to the sensors with conventional and inexpensive, gas-permeable hoses and no special, in particular structural, measures are required for producing the calibration fluid with the predetermined other concentration of the gas differing from the concentration of this gas in the predetermined calibration fluid. Many inexpensive hoses have inadequate gas impermeability which normally precludes their use, but in this embodiment the permeability of the inexpensive hoses is exploited as a prerequisite for the implementation of this version of the method. Moreover, there is the advantage that both the predetermined (first) calibration fluid and the (second) calibration fluid with the predetermined, other concentration that is produced from this first calibration fluid are supplied to the sensor in the same hose, so that a single hose advantageously suffices for supplying the two calibration fluids to the sensor.

Preferably, the predetermined calibration fluid is taken from a gas-impermeable vessel. The hose for delivering the calibration fluids to the sensor can be connected to this vessel. The vessel can be a gas-impermeable bag that is preferably a metalcoated plastic bag. The predetermined calibration fluid can be taken from the vessel with a pump, for example a dosing pump.

Although not limited thereto, the inventive method can be applied to sensors that generate a measured value proportional to a logarithm of the concentration or of the partial pressure of the gas dissolved in the liquid, as well as to sensors that generate a measured value directly proportional to the concentration or partial pressure of the gas dissolved in the liquid.

It is often the case that the concentration or the partial pressure of the gas dissolved in a calibration fluid is a defined, non-constant function of the pH value of this calibration fluid. Such a predetermined calibration fluid, for example, plays a part in an embodiment described below for determining the $CO_2$ concentration of blood.

In such a case, it is generally expedient when the predetermined, other concentration of the (second) calibration fluid produced from the predetermined (first) calibration fluid, for example by material transport or gas exchange between the gas phase and the predetermined calibration fluid, is determined by identifying the pH value of the second calibration fluid produced in this way.

In this context, it is possible in certain cases to employ a predetermined calibration fluid wherein a logarithm of the concentration of the gas dissolved in this calibration fluid is a non-constant, linear function f of the variable pH value of this calibration fluid. An example of such a calibration fluid is an aqueous solution (described below) in which $CO_2$ and bicarbonate, i.e. $HCO_3^{31}$, are dissolved and that contains no further pH-buffering substances other than this buffer system.

In the wherein the sensor generates a measured value proportional to a logarithm of the concentration of the gas dissolved in the liquid, the predetermined calibration fluid and the further calibration fluid having the predetermined, other concentration of the gas in question (produced from the predetermined calibration fluid) are supplied to pH sensor, which generates respective measured values corresponding to the different pH values of the two calibration fluids. A calibration quantity $K_{pG}$ is then formed using the aforementioned concentration values $U_{pG}(C)-U_{pG}(C')$ obtained from the sensor to be calibrated according to the formula $$K_{pG}=(U_{pG}(C)-U_{pG}(C'))/(U_{pH}(C)-U_{pH}(C'))$$

wherein $U_{pH}(C)$ and $U_{pH}(C')$ are the respective pH values obtained from the pH sensor.

The inventive method is fundamentally employable for all dissolved gases for which there are sensors with which the concentration or the partial pressure of these dissolved gases can be measured. In addition to the sensor for measuring the concentration of $CO_2$ dissolved in liquid, sensors for measuring the concentration of $NH_3$, $SO_2$, $NO_2$ or $H_2S$ dissolved in liquid are examples of sensors that generate a measured value proportional to the logarithm of the gas concentration.

Gases that are dissolved in a physiological body fluid or in a physiological tissue are of particular significance, including $CO_2$ dissolved in blood. Accordingly, in the inventive method the sensor which is used to measure the partial pressure can be a $CO_2$ sensor, which measures the partial pressure of $CO_2$ dissolved in a fluid as an indicator $CO_2$ concentration in the fluid. The sensor employed in the inventive method can also be a sensor for measuring the partial pressure of a gas dissolved in a physiological body fluid and/or physiological tissue, as an indicator of the concentration of the gas in the body fluid or tissue.

The inventive calibration method according to this last-described embodiment can be especially advantageously applied for measuring the concentration of $CO_2$ dissolved in blood with a $CO_2$ sensor for measuring the $CO_2$ concentration and generating a measured value proportional to the logarithm of the $CO_2$ concentration. Another embodiment of the inventive method for concentration measurement of $CO_2$ in blood is a solution to the following problem:

Substances dissolved in blood, including the blood gases $N_2$, $O_2$ and $CO_2$ and non-volatile, other substances, including $K^+$, $Ca^{2+}$ and biomolecules such as glucose, lactate, etc., and the pH value of the blood if necessary, are measured by sensors allocated to these substances, whereby a base line fluid that is contained in a preferably gas-tight vessel and is preferably pH-buffered and a calibration fluid contained in another gas-tight vessel are employed, these containing the blood substances to be measured dissolved in respectively optimally exactly defined physiological concentrations and each having a respectively optimally exactly defined physiological pH value as warranted.

The "physiological concentration" of a substance means any concentration at which this substance occurs in a living organism, whether in a body fluid or in tissue of the organism and/or whether in a healthy or pathological organism. Correspondingly, the physiological pH value means any pH value that occurs in the living organism, whether in a body fluid or in the tissue of the organism and/or whether in a healthy or pathological organism.

For example, the physiological concentration of $CO_2$ in human blood lies between a partial pressure of 10 Torr and 150 Torr, whereby 1 Torr is equal to 133.3224 Pa and approximately equal to 1 mmHg. The physiological pH value of this blood lies between 6.8 and 7.8.

The "normal physiological concentration" of a substance means any physiological concentration of this substance normally occurring in a healthy organism. Correspondingly, the normal physiological pH value is any physiological pH value normally occurring in the healthy organism.

For example, the normal physiological concentration of $CO_2$ in human blood lies between a partial pressure of 35 Torr and 45 Torr. The normal physiological pH value of this blood lies between 7.35 and 7.45.

For measurement, each sensor is supplied, for example in alternation, with the base line fluid from its vessel and, for example, the arterial blood, whereby this sensor measures the concentration or partial pressure of the substance appertaining thereto in the base line fluid and in the blood.

Each sensor is additionally calibrated with the assistance of the calibration fluid in which the substances contained in the base line fluid must be dissolved in a concentration different from the base line fluid and that, as warranted, must have a pH value differing from the pH value of the base line fluid. After first-time calibration, a recalibration can be undertaken from time to time with this calibration fluid.

A problem arises when the concentration or the partial pressure of $CO_2$ dissolved in blood is to be measured and an aqueous solution that is air-saturated under normal conditions, i.e. at room temperature and normal atmospheric pressure, is employed as the base line fluid. Under normal conditions, $CO_2$ is contained in air with a partial pressure of less than 1 Torr. The base line fluid saturated with this air contains the dissolved $CO_2$ in a concentration that is equal to the partial pressure of the $CO_2$ in air that amounts to less than 1 Torr. This $CO_2$ concentration of the base line fluid thus lies far below the lower limit of the physiological concentration of $CO_2$ in blood that lies at a partial pressure of about 10 Torr. Moreover, the $CO_2$ concentration of the air-saturated base line fluid is usually not known with adequate precision.

For these reasons, such an air-saturated base line fluid cannot be utilized for calibrating the $CO_2$ sensor.

In order nonetheless to be able to calibrate the $CO_2$ sensor in this case, a second calibration fluid would have to be employed in addition to the first calibration fluid, this second calibration fluid containing the dissolved $CO_2$ in a physiological concentration that is exactly defined but clearly different from that of the one calibration fluid and, as warranted, having a physiological pH value that is clearly different from that of the first calibration fluid but that is exactly defined. This second calibration fluid would have to be contained in an additional gas-tight vessel, as a result the complexity, and thus the costs, for the $CO_2$ measuring apparatus would be increased in an unacceptable way.

Since the second required calibration fluid is acquired in the inventive method in a simple way from the first, i.e. the predetermined calibration fluid, using the inventive method for measuring the $CO_2$ concentration in blood advantageously only requires one gas-tight vessel for the predetermined calibration fluid in addition to the gas-tight vessel for the base line fluid, so that a conventional apparatus can be employed without modification for the implementation of the inventive method for measuring the concentration of substances dissolved in blood using a base line fluid and a calibration fluid.

The invention is especially well-suited for on-line blood gas monitoring systems.

DESCRIPTION OF THE PREFERRED EMBODIMENTS

Figure 1:
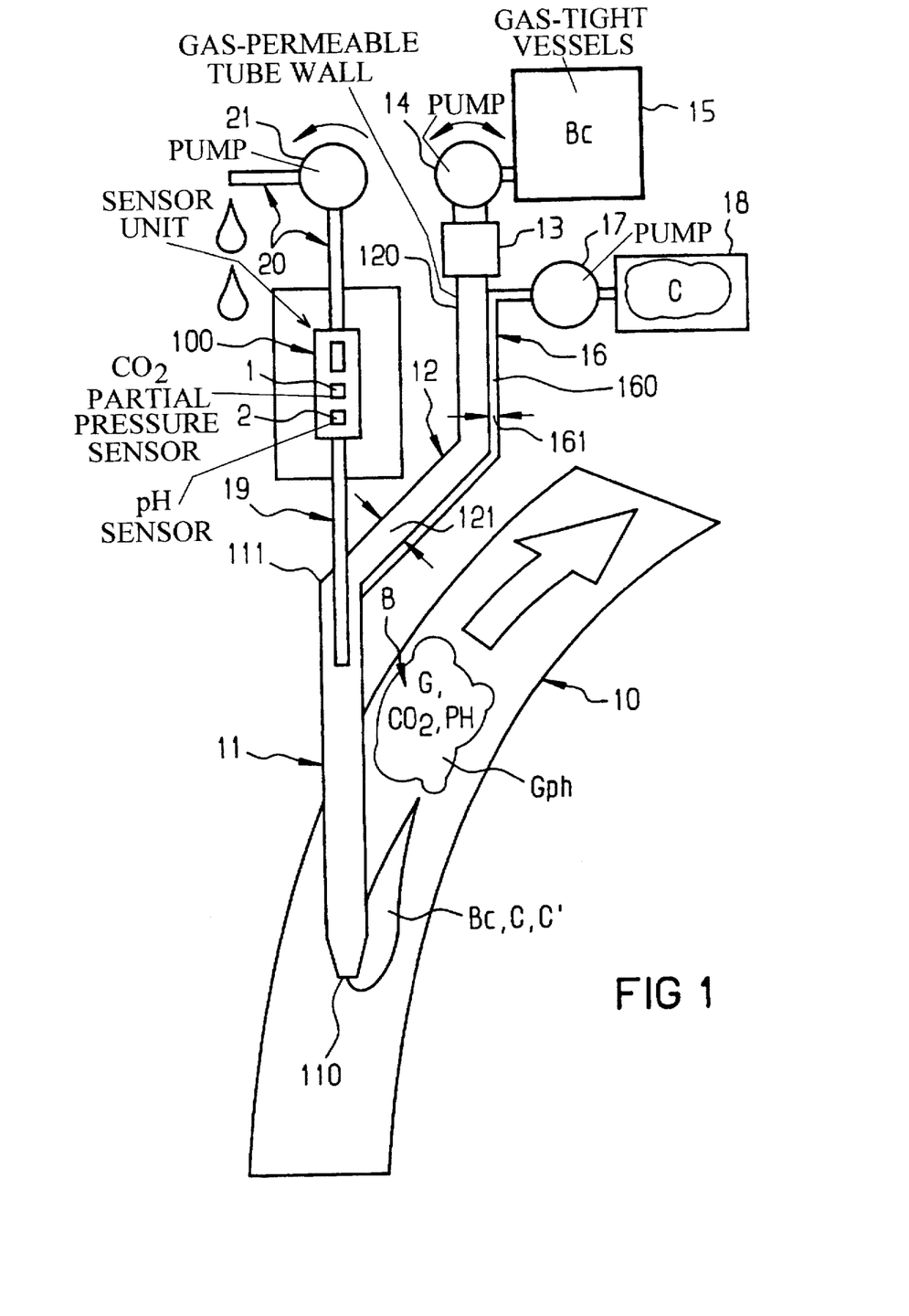
FIG. 1 is a schematic illustration of a known apparatus for the implementation of a method for measuring the concentration of substances dissolved in blood using a base line fluid and a calibration fluid.

The exemplary apparatus shown in FIG. 1 has a cannula 11 which is introduced into a blood vessel 10, for example an artery, and which has an open tip 110 located within the blood vessel 10 in the blood B flowing therein, and an open end 111 located outside the blood vessel 10.

The end 111 is connected via a tube (hose) 12 having a gas-permeable tube wall 120, and a pump 14 to a gas-tight vessel 15 containing a base line fluid BF. The end 111 is also connected via a tube (hose) 16, having a gas-permeable hose wall 160 and a pump 17 to a gas-tight vessel 18 containing the predetermined calibration fluid C.

A liquid channel 19, for example likewise a gas-permeable hose, leads from the inside of the cannula 11 to a sensor unit 100 that at least contains a $CO_2$ sensor 1. In addition to the $CO_2$ sensor 1, however, the sensor unit 100 may contain one or more sensors for measuring the partial pressure or the concentration of specific, other volatile and/or non-volatile substances contained in the blood B, for example for the substances $O_2$, $K^+$, $Ca^{2+}$, lactate, etc. recited later and/or a pH sensor 2.

A liquid channel 20 leads from the sensor unit 100 via a pump 21 to a receptacle vessel (not shown) for liquid measured by the sensors that can be disposed of.

For measuring the concentration of a gas G other than $CO_2$, a non-volatile substance, or the pH value pH(B) of the blood, the base line fluid BF from the vessel 15 and the blood B from the blood vessel 10 are supplied in alternation to a sensor in the sensor unit 100 that is allocated to this gas G, non-volatile substance or pH value.

The delivery of the base line fluid BF to the appropriate sensor ensues such that this fluid BF is drawn by suction from the vessel 15 by the pump 14 and is pumped through the gas-permeable hose 12 into the cannula 11, so that the cannula 11 becomes completely filled with the base line fluid BF, causing blood B contained in the cannula 11 to be displaced from the cannula 11 through the tip 110 thereof into the blood vessel 10.

The fluid BF is drawn through the liquid channel 19 by the pump 21 from the cannula 11 now filled only with the base line fluid BF, and is conveyed to the sensor unit 100 in which the exactly defined concentration of the gas G, or non-volatile substance contained in the base line fluid BF, or the exactly defined pH value of this fluid BF, is measured by the allocated sensor.

The base line fluid BF measured in the sensor unit 100 is conveyed through the liquid channel 20 to the collecting vessel by the pump 21 and is collected therein, for example for waste disposal.

When the delivery of base line fluid BF from the vessel 15 into the hose 12 is completed, the blood B is supplied to the sensor unit 100 by means of the pump 14 suctioning blood B from the blood vessel 10 into the cannula 11 through the open tip 110 thereof until the cannula 11 becomes completely filled with blood B, and the pump 21 then conveys the blood B from the blood-filled cannula 11 through the liquid channel 19 to the sensor unit 100 in which the concentration of the gas G, or non-volatile substance, and/or the pH value of the blood B, is measured by the respectively allocated sensor.

The blood B measured in the sensor unit 100 is conveyed through the liquid channel 20 to the collecting vessel by the pump 21 and is collected therein, for example for waste disposal.

For a calibration of the appertaining sensor, a predetermined calibration fluid C is drawn by suction from the vessel 18 by the pump 17 and is conveyed through the gas-permeable hose 16 into the cannula 11 until the cannula 11 becomes completely filled with the predetermined calibration fluid C, and blood B or base line fluid BF contained in the cannula 11 is displaced through the tip 110 thereof into the blood vessel 10.

The fluid C is drawn through the liquid channel 19 by the pump 21 from the cannula 11, now filled only with the predetermined calibration fluid C, and is conveyed to the sensor unit 100 in which the exactly defined concentration of the gas G, or non-volatile substance contained in the calibration fluid C, or the exactly defined pH value of this fluid C, is measured by the allocated sensor.

The calibration fluid C measured in the sensor unit 100 is conveyed through the channel 20 to the collecting vessel by the pump 21 and is collected therein, for example for waste disposal.

When the concentration of $CO_2$ in the blood B is to be measured, the gas permeability of the respective hose walls 120 and 160 of the two hoses 12 and 16 is exploited, particularly the gas permeability of the hose wall 160. These gas-permeable hose walls 12 and 16 enable a gas exchange or material transport between the fluid contained in the hose 12 or 16 and a medium that surrounds the hose wall 120 or 160 at its exterior, for example the gas phase Gph that leads to a desired change in the concentration or of the partial pressure of the $CO_2$ or of another gas G that is dissolved in a liquid contained in the hose 12 or 16.

Ambient air, i.e. the air of the room in which the measuring instrument is placed, is advantageously employed as the surrounding gas phase Gph. At room temperature, i.e. at 20° through 23° C., and normal atmospheric pressure at a normal level, i.e. at 720 through 760 Torr, the ambient air contains the $CO_2$ with a partial pressure of less than 1 Torr.

By contrast, a calibration fluid C is employed in which $CO_2$ is dissolved with an exactly defined physiological partial pressure $pCO_2(C)$.

As described above, the base line fluid BF is brought to the $CO_2$ sensor through the hose 12. A longer dwell time of the base line fluid BF in the gas-permeable hose 12 is allowed, and may be desirable, since the $CO_2$ partial pressures $pCO_2$ (BF) or $pCO_2$(Gph) of the base line fluid BF and of the ambient room air Gph have similar values, and the $CO_2$ partial pressure $CO_2$(BF) of the base line fluid BF would at most adapt to the $CO_2$ partial pressure $pCO_2$(Gph) of the room air Gph due to material transport or gas exchange with a longer dwell time, and consequently changes occur only slightly or are defined over a constant dwell time.

For these reasons, a hose 12 can be employed having a lumen 121 that is over-dimensioned with reference to a quantity of base line fluid BF to be delivered to the $CO_2$ sensor 1 in a specific time duration.

The relatively large lumen 121 can be a part of a pressure transducer 13 integrated in the liquid channel for the base line fluid BF that leads from the vessel 15 to the cannula 11, and which contains the hose 12, thereby enabling transmission of the medically significant arterial pressure amplitudes.

The conditions are different in the case of the predetermined calibration fluid C. The $CO_2$ is dissolved in the predetermined calibration fluid C with an exactly defined physiological partial pressure $pCO_2$(C) that is significantly higher than the $CO_2$ partial pressure $pCO_2$(Gph) of the ambient air Gph.

To insure that no change of the exactly defined $CO_2$ partial pressure $pCO_2$(C) of this fluid C beyond a prescribable, allowed amount occurs due to the higher $CO_2$ partial pressure difference between the predetermined calibration fluid C and the ambient air Gph, this fluid C can remain in the gas-permeable hose 16 for at most a short dwell time defined by this amount.

For this reason, the hose 16 must have a lumen 161 dimensioned small with reference to a quantity of predetermined calibration fluid C to be delivered to the sensor unit 100, or the $CO_2$ sensor 1, in a defined time duration such that the calibration fluid C experiences no change in the concentration $pCO_2$(C) of the $CO_2$ dissolved in this fluid C that goes beyond the prescribable allowed amount during delivery to the sensor unit 100 or to the $CO_2$ sensor 1.

The second calibration fluid required for calibration of the $CO_2$ sensor 1 is inventively produced by material transport or gas exchange between the predetermined calibration fluid C and the ambient air Gph, by allowing $CO_2$ temporarily to outgas from the predetermined calibration fluid C into the ambient air Gph under the existing conditions. To that end, the calibration fluid C' with the predetermined, other concentration $pCO_2$(C') of $CO_2$ is produced from the predetermined calibration fluid C by temporarily allowing the predetermined calibration fluid C to dwell in the hose 16 and by allowing the $CO_2$ to outgas from the predetermined calibration fluid C through the hose wall 160 into the ambient air Gph.

The determination of the other concentration $pCO_2$(C') of the calibration fluid C' produced from the predetermined calibration fluid C by material transport or gas exchange can ensue with a pH measurement when a predetermined calibration fluid C is employed wherein a logarithm of the concentration $pCO_2$(C) of the $CO_2$ dissolved in this calibration fluid C is a defined, non-constant function f of the variable pH value pH(C) of this calibration fluid. In this case, the defined other concentration $pCO_2$(C') of the produced calibration fluid C' can be determined with the pH sensor 2 of the sensor unit 100 that has already been calibrated by means of the pH value of the base line fluid BF and of the predetermined calibration fluid C.

Using the pH value pH(C') determined by the pH sensor 2 for the calibration fluid C' produced from the predetermined calibration fluid C, the logarithm of the other $CO_2$ concentration $pCO_2$(C') of this produced calibration fluid C' can be determined by $$\log(pCO_2(C'))=f(pH(C'))$$

and this identified logarithm can be allocated to the measured value $U_{CO2}$(C') measured by the $CO_2$ sensor 1.

When, however, the calibration fluid only contains the buffer system composed of carbon dioxide and $HCO_3^-$ and no other pH-buffering substances, $\log(pCO_2)$ is a linear function of the pH value pH that is established by $$\log(pCO_2(C'))=pH(C)-pH(C')+\log(pCO_2(C)).$$

In this case, a two-point calibration suffices for calibrating the $CO_2$ sensor 1, i.e. only another $CO_2$ concentration $p_{CO2}$(C') of a calibration fluid C' need be identified in addition to the exactly defined $CO_2$ concentration $p_{CO2}$(C) of the predetermined calibration fluid.

Expediently, a calibration quantity $K_{pCO2}$ is formed by $$-K_{pCO2}=(U_{pCO2}(C)-U_{pCO2}(C'))/(U_{pH}(C)-U_{pH}(C'))$$

in this case.

In this case, a method for measuring the concentration or the partial pressure $pCO_2$(B) of $CO_2$ dissolved in the blood is expediently implemented with a $CO_2$ sensor 1 for measuring the $CO_2$ concentration $pCO_2$ and for generating a corresponding measured value $U_{pCO2}$ proportional to the logarithm of the $CO_2$ concentration $pCO_2$, such that successively, in an arbitrary sequence, the $CO_2$ sensor 1 and pH sensor 2 are supplied with the predetermined calibration fluid C in which the $CO_2$ is dissolved with an exactly defined physiological partial pressure $pCO_2$(C) and in which $HCO_3^1$ is dissolved with an exactly defined physiological concentration $HCO_3^-$ and which has an exactly defined physiological pH value pH(C), and the calibration fluid C' produced from the predetermined calibration fluid C by the gas exchange between this fluid C and the defined gas phase Gph, this calibration fluid C' differing from the predetermined calibration fluid C only on the basis of the physiological $CO_2$ partial pressure $pCO_2$(C') differing from the $CO_2$ partial pressure $pCO_2$(C) of the predetermined calibration fluid C and the physiological pH value pH(C') produced solely by this difference thus also differing from the pH value pH(C) of the predetermined calibration fluid C, and the pH sensor 2 is also supplied with a base line fluid BF in which $CO_2$ is dissolved with a concentration $PCO_2$(BF) corresponding to a partial pressure of less than 10 Torr and that has a defined physiological pH value pH(BF) differing from the pH value pH(C) of the predetermined calibration fluid C, and the measured value $U_{pCO2}$(C) corresponding to the $CO_2$ partial pressure $pCO_2$(C) of the predetermined calibration fluid C, the measured value $U_{pCO2}$(C') corresponding to the $CO_2$ partial pressure $pCO_2$(C') of the calibration fluid C' produced from the predetermined calibration fluid C, the measured value $U_{pH}(C)$ corresponding to the pH value pH(C) of the predetermined calibration fluid C, the measured value $U_{pH}(C')$ corresponding to the pH value pH(C') of the calibration fluid C' produced from the predetermined calibration fluid C, as well as the measured value $U_{pH}(BF)$ corresponding to the pH value pH(BF) of the base line fluid BF are determined.

With these determined measured values $U_{pCO2}(C)$, $U_{pCO2}(C')$, $U_{pH}(C)$, $U_{pH}(C')$ and $U_{pH}(BF)$ and with the defined pH values pH(C) and pH(BF) of the predetermined calibration fluid C and base line fluid BF itself, the quantity $$S_{pCO2}=K_{pCO2}\cdot S_{pH} \text{ is formed}$$

with $K_{pCO2}=-[(U_{pCO2}(C)-U_{pCO2}(C'))/(U_{pH}(C)-U_{pH}(C'))]$ and $S_{pH}=(\Delta U_{pH}(C))/(pH(C)-pH(BF))$ with $$\Delta U_{pH}(C)=U_{pH}(C)-U_{pH}(BF)$$

With the quantity $S_{pCO2}$ the $CO_2$ partial pressure $pCO_2(B)$ of $CO_2$ dissolved in the blood can be determined using a measured value $U_{pCO2}(B)$ that is determined by supplying blood B to the $CO_2$ sensor 1 and that corresponds to the $CO_2$ partial pressure $pCO_2(B)$ of the blood B, a measured value $U_{pCO2}(BF)$ that is determined by delivering base line fluid BF to the $CO_2$ sensor 1 and that corresponds to the $CO_2$ partial pressure $pCO_2(BF)$ of the base line fluid BF on the basis of $$log(pCO2(B))=(\Delta U_{pCO2}(B)-\Delta U_{pCO2}(C))/S_{pCO2}+log(pCO_2(C))$$

with $\Delta U_{pCO2}(B)=U_{pCO2}(B)-U_{pCO2}(BF)$ and $\Delta U_{pCO2}(C)=U_{pCO2}(C)-U_{pCO2}(BF)$.

The predetermined calibration fluid C and any calibration fluid C' produced therefrom should generally have normal physiological partial pressure or concentration values and pH values in all of its components, including $CO_2$.

As indicated above, the $CO_2$ partial pressure pCO2(BF) of the base line fluid BF in the hose 12 can continuously change slightly due to dwell times of different lengths in the hose 12 and/or the non-constant atmospheric pressure of the ambient room air Gph, i.e. the $CO_2$ partial pressure $pCO_2$(BF) of the base line fluid BF delivered to the $CO_2$ sensor can drift.

In case the $CO_2$ partial pressure $pCO_2$(BF) of the base line fluid BF changes over the course of time t the quantity $\Delta U_{pCO2}(C)$ is formed by $$\Delta U_{pCO2}(C)=U_{pCO2}(C)-U_{pCO2}(BF(t_c))$$

with a measured value $U_{pCO2}(BF(t_c))$ of the $CO_2$ partial pressure $pCO_2$(BF) of the base line fluid BF measured close in time to the $CO_2$ measurement undertaken at the predetermined calibration fluid C and the quantity $\Delta U_{pCO2}(B)$ is formed by $$\Delta U_{pCO2}(B)=U_{pCO2}(B)-U_{pCO2}(BF(t_b))$$

with the assistance of a measured value $U_{pCO2}(BF(t_b))$ of the $CO_2$ partial pressure $pCO_2$(BF) of the base line fluid BF measured close in time to the $CO_2$ measurement undertaken at the blood B.

The pH value pH(BF) of the base line fluid BF should be defined as exactly as possible and should remain constant over time, so that it need not be constantly measured. In order to enable this, the base line fluid BF should be pH-buffered. The buffering substances should be physiologically compatible. Suitable substances are certain phosphate compounds such as, for example, hydrogen phosphate $HPO_4^{--}$, dihydrogen phosphate $H_2PO_4^-$, organic phosphate, etc.

In case, however, that the defined pH value pH(BF) of the base line fluid BF also drifts, similar to the $CO_2$ partial pressure $pCO_2$ thereof, the method can proceed with the quantities $\Delta U_{pH}(C)$ and $\Delta U_{pH}(C')$ required for the quantity $S_{pH}$ being formed by $$\Delta U_{pH}(C)=U_{pH}(C)-U_{pH}(BF(t_c))$$

$$\Delta u_{pH}(C')=U_{pH}(C)-U_{pH}(BF(t_c))$$

with a measured value $U_{pH}(BF(t_c))$ of the pH value pH(BF (t$_c$)) of the base line fluid (BF) measured close in time to the $CO_2$ measurement undertaken at the predetermined calibration fluid C.

Figure 2:
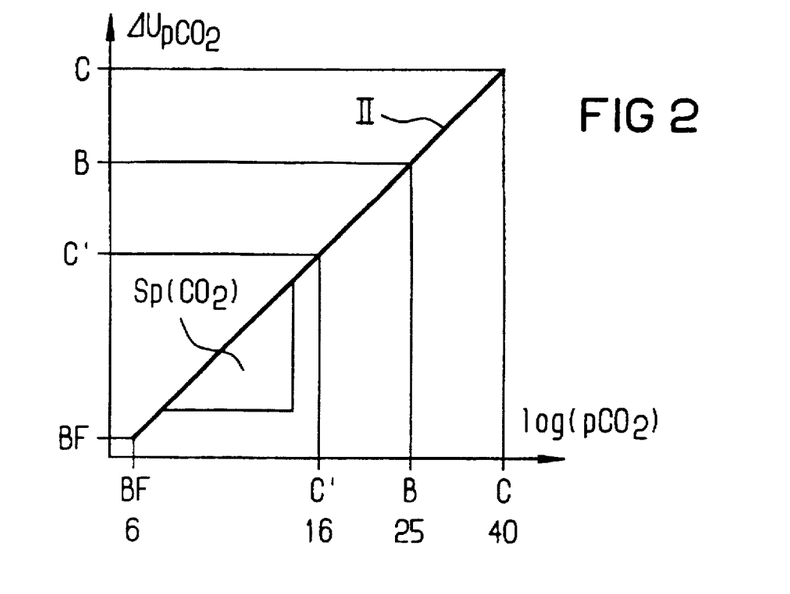
FIG. 2 shows the difference $\Delta U_{pCO2}$ between a measured value $U_{pCO2}$ of the $CO_2$ sensor measured at a liquid to be analyzed and the measured value $U_{pCO2}(BF)$ of the $CO_2$ sensor measured at the base line fluid dependent on the logarithm $\log(pCO_2)$ of the partial pressure $pCO_2$ of the $CO_2$ dissolved in the liquid to be analyzed.

As an example, FIG. 2 shows a diagram of a characteristic of a $CO_2$ sensor 1 for measuring the concentration or the partial pressure $pCO_2$ of $CO_2$ dissolved in a liquid. This diagram shows the $CO_2$ measured value of the sensor 1 referred to the $CO_2$ measured value $U_{pCO2}$(BF) of a base line fluid, i.e. shows the quantity or difference $\Delta u_{pCO2}$, dependent on log(pCO$_2$) for an exemplary range of log(pCO$_2$) that corresponds to a $CO_2$ partial pressure range from 0 to somewhat above 40 Torr. The relationship between $\Delta U_{pCO2}$ and log(pCO$_2$) is indicated by the line II with the slope $S_{pCO2}$.

It is assumed, for example, in FIG. 2 that pCO$_2$(BF)=6 Torr, pCO$_2$(B)=25 Torr, pCO$_2$(C)=40 Torr and pCO$_2$(C')=16 Torr.

Figure 3:
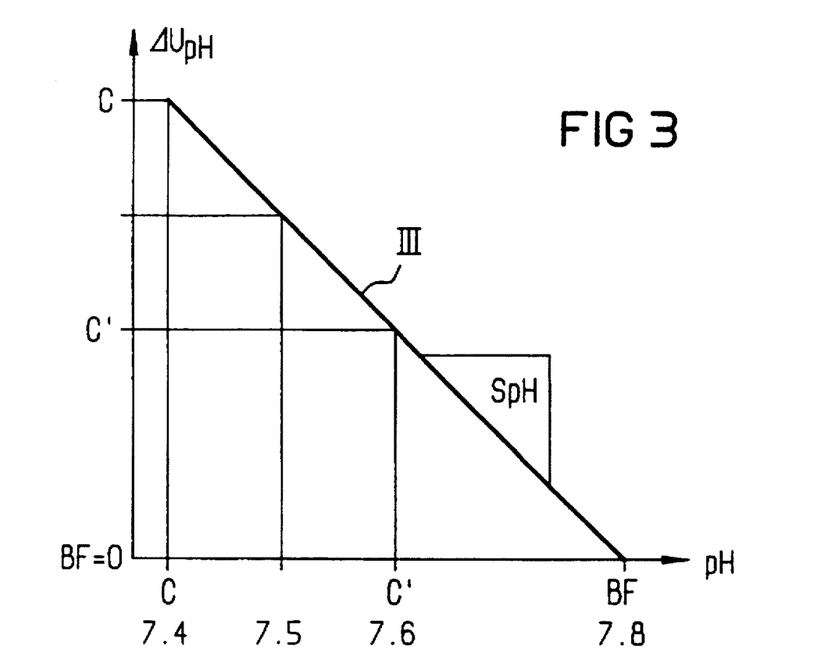
FIG. 3 shows the difference $\Delta U_{pH}$ between a measured value $U_{pH}$ of the pH sensor measured at a liquid to be analyzed and the measured value $U_{pH}(BF)$ of the pH sensor measured at the base line fluid dependent on the pH value of the liquid to be analyzed.

As an example, FIG. 3 shows a diagram of a characteristic of a pH sensor 2 for measuring the pH value of a liquid. This diagram shows the pH measured value of the sensor 2 referred to the pH measured value $U_{pH}$(BF) of a base line fluid, i.e. shows the quantity or difference $\Delta U_{pH}$, dependent on the pH value for an exemplary pH range from 7.0 to 7.8. The relationship between $\Delta U_{pH}$ and the pH value is indicated by the line III with the slope $S_{pH}$.

It is assumed, for example, in FIG. 3 that pH(BF)=7.8, pH(B)=7.5, pH(C)=7.4 and pH(C')=7.6.

Figure 4:
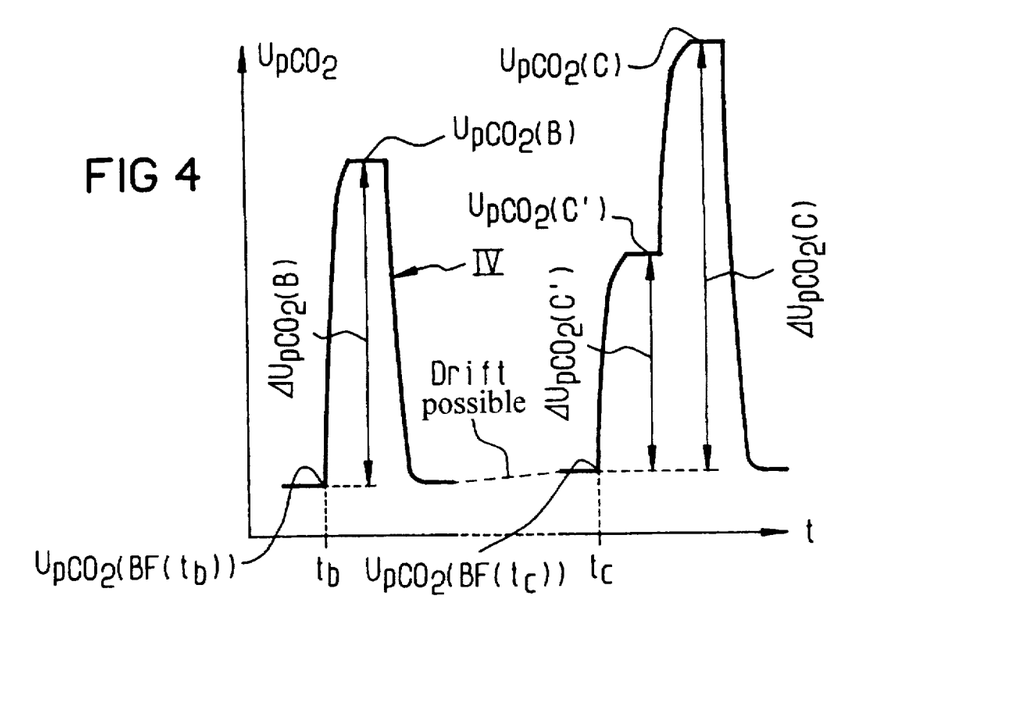
FIG. 4 shows a measured curve recorded by the $CO_2$ sensor using the inventive method for measuring the $CO_2$ concentration in blood with the apparatus of FIG. 1 and showing the time curve of the measured value $U_{pCO2}$.

FIG. 4 shows a measured curve IV registered in the above-recited inventive method for measuring the $CO_2$ concentration of blood B with the $CO_2$ sensor 1 that illustrates the curve of the measured value $U_{pCO2}$ supplied by this sensor over the time t.

Figure 5:
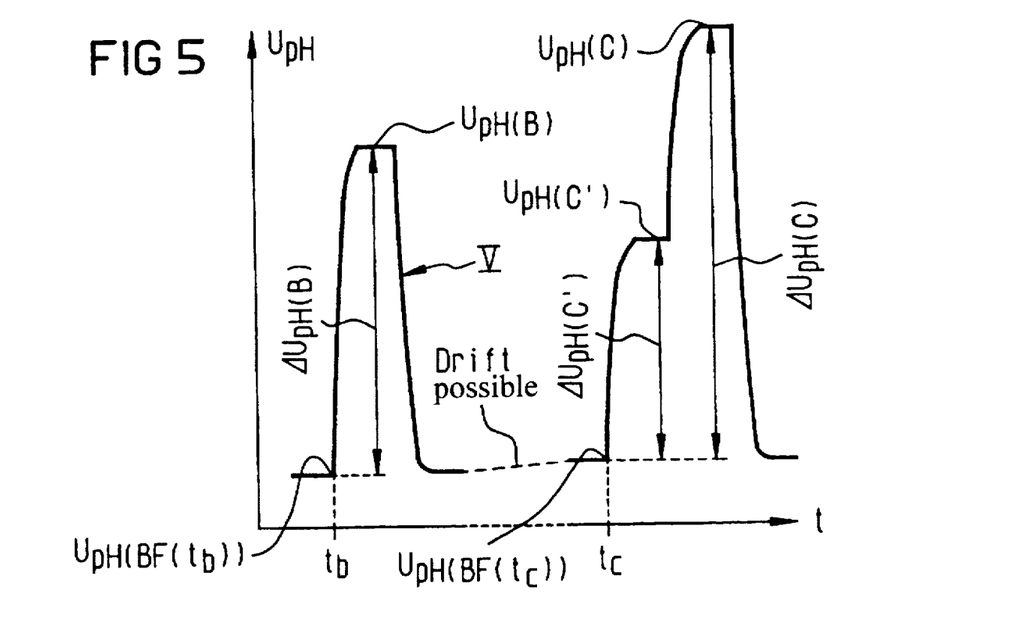
FIG. 5 is a measured curve recorded by the pH sensor using the inventive method for measuring the $CO_2$ concentration in blood with the apparatus of FIG. 1 and showing the time curve of the measured value $U_{pH}$ of this sensor.

FIG. 5 shows a measured curve V registered in this method with the pH sensor 2 that shows the curve of the measured value $U_{pH}$ supplied by this sensor 2 over the t. In this FIG, $\Delta U_{pH}$(B) denotes the difference $U_{pH}$(B)−$U_{pH}$(BF).

The relationships that can be derived from FIGS. 2 through 5 are based essentially on the following actual exemplary embodiment of this inventive method for measuring the $CO_2$ concentration of blood B.

In this actual exemplary embodiment, a pH-buffered base line fluid BF in the form of an air-saturated aqueous solution was used which, at 37° C., included an exactly defined physiological pH value pH(BF) of, for example, 7.8, $O_2$ with a physiological partial pressure $pO_2$(BF) of about 185 Torr, $CO_2$ with an imprecisely defined partial pressure $pCO_2(BF)$ of less than 10 Torr, $K^+$ in an exactly defined concentration $cK^+(BF)$ of, for example, 2.0 mmol/l, $Ca^{2+}$ in an exactly defined concentration $cCa^{2+}(BF)$ of, for example, 1.0 mmol/l, and lactate in an exactly defined concentration $cL(BF)$ of, for example, 0.0 mmol/l, and a predetermined calibration fluid C in the form of an aqueous solution was used which, at 37° C., included an exactly defined physiological pH value $pH(BF)$ of, for example, 7.40, $O_2$ with an exactly defined physiological partial pressure $pO_2(C)$ of, for example, 185 Torr, $CO_2$ with an exactly defined physiological partial pressure $pCO_2(C)$ of, for example, 40 Torr, $K^+$ in an exactly defined concentration $cK^+(BF)$ of, for example, 4.0 mmol/l, $Ca^{2+}$ in an exactly defined concentration $cCa^{2+}(BF)$ of, for example, 2.0 mmol/l, and lactate in an exactly defined concentration $cL(BF)$ of, for example, 5.0 mmol/l.

A measurement at the blood B was implemented about every 2 to 3 minutes. For the blood B as well as the base line fluid, each of these measurements encompassed at least the acquisition of $U_{pCO2}(B)$, $U_{pCO2}(BF)$ but can also include the acquisition of $U_{pH}(B)$ and $U_{pH}(BF)$ and/or one or more of the other above substances contained in the blood B and the base line fluid BF.

$U_{pH}(BF)$ need only be determined once since the base line fluid BF is buffered and $pH(BF)$ is constant over time. Otherwise, $U_{pH}(BF)$ must also be determined more or less often dependent on drift.

$U_{pCO2}(BF)$ should be acquired at a point in time $t_b$ lying close to a measurement undertaken at the blood B. The same is true when $U_{pH}(BF)$ is to be determined and $pH(BF)$ drifts.

A measurement at the predetermined calibration fluid C for a calibration of the sensors was implemented about every 1 to 3 hours. For the predetermined calibration fluid C as well as the base line fluid BF, each of these measurements encompassed at least the acquisition of $U_{pCO2}(C)$, $U_{pCO2}(BF)$, $U_{pH}(C)$ but can also include the acquisition of measured values of one or more of the other above substances contained in the predetermined calibration fluid C and the base line fluid BF. $U_{pH}(BF)$ must also be acquired now, at the latest, since this measured value is required for calibrating the $CO_2$ sensor.

In the calibration, $U_{pCO2}(BF)$ should be acquired at a point in time $t_c$ lying close to a measurement undertaken at the predetermined calibration fluid C. The same is true of $U_{pH}(BF)$ when $ph(BF)$ drifts.

The base line fluid BF was supplied to the sensors 1 and 2 through a hose 12 having a length, for example, of 1 to 2 m and a lumen 121 of, for example, 1.5 mm. The dwell time of the base line fluid BF in this hose 12 thereby amounted, for example, to 30 min.

The predetermined calibration fluid C was supplied to the sensors 1 and 2 through a hose 16 having a length, for example, of 1 to 2 m and a lumen 161 of, for example, 0.5 mm. The dwell time of the calibration fluid C in this hose 16 amounted to a few seconds.

$U_{pCO2}(C')$ and $U_{pH}(C')$ are acquired a short time before the measurement at the predetermined calibration fluid C when the calibration fluid, which remained in the hose 16 for a longer time since the last measurement at the predetermined calibration fluid and from which $CO_2$ has outgassed and which forms the calibration fluid C' with the other concentration $pCO_2(C')$ acquired from the predetermined calibration fluid, is supplied to the $CO_2$ sensor 1 as well as to the pH sensor 2.

Thereafter, all measured values required for the exact determination of $\log(pCO_2(B))$ have been acquired and $pCO_2(B)$ can be identified since $pCO_2(C)$ is exactly known.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for calibrating a sensor for measuring a concentration of gas dissolved in a fluid and for generating a measured value corresponding to the measured concentration, comprising the steps of:

providing a predetermined, first calibration fluid having a predetermined, first concentration of a gas dissolved therein;

providing a gas phase containing the same gas as is dissolved in said first calibration fluid, said gas in said gas phase being at a partial pressure in said gas phase differing from said partial pressure of said gas in said first calibration fluid, so that a partial pressure difference for said gas exists between said gas phase and said first calibration fluid;

separating said gas phase from said fist calibration fluid by a gas-permeable wall;

forming a second calibration fluid from said first calibration fluid by modifying the concentration of said gas in said first calibration fluid to a predetermined, second concentration of said gas in said second calibration fluid exclusively by causing a material transport between said first calibration fluid and said gas phase through said gas-permeable wall by virtue of said partial pressure difference, said second concentration being different from said first concentration;

supplying said first and second calibration fluids to a sensor to be calibrated; and calibrating said sensor by identifying first and second measured values using said sensor corresponding said first and second concentrations.

2. A method as claimed in claim 1 wherein the step of causing a material transport includes:

adjusting said partial pressure difference until said predetermined, second concentration in said second calibration fluid is present.

3. A method as claimed in claim 1 wherein said gas phase comprises air.

4. A method as claimed in claim 1 wherein the step of causing a material transport comprises:

supplying said first calibration fluid to said sensor through a tube having a gas-permeable tube wall, comprising said gas-permeable wall, surrounded at an exterior by said gas phase and having an interior cross-section which is small relative to a quantity of said first calibration fluid to be delivered to said sensor per unit of time for preventing modification of said first concentration of said gas in said first calibration fluid beyond a prescribed amount due to said material transport during delivery of said first calibration fluid to said sensor; and producing said second calibration fluid from said first calibration fluid by allowing said first calibration fluid to temporarily dwell in said tube thereby producing a defined material transport between said first calibration fluid in said tube and said gas phase via said tube wall.

5. A method as claimed in claim 4 wherein the step of supplying said first calibration fluid to said sensor via said tube is further defined by supplying said first calibration fluid from a gas-impermeable vessel to said sensor via said tube.

6. A method as claimed in claim 1 wherein the step of calibrating said sensor comprises generating in said sensor respective measured values which are directly proportional to the respective concentrations of said gas in said first and second calibration fluids supplied to said sensor.

7. A method as claimed in claim 1 wherein the step of calibrating said sensor comprises generating in said sensor respective measured values which are proportional to a logarithm of the respective concentrations of said gas in said first and second fluids supplied to said sensor.

8. A method as claimed in claim 1 wherein the step of providing said predetermined, first calibration fluid comprises providing a predetermined, first calibration fluid having a first concentration of said gas dissolved therein which is a defined, non-constant function of a variable pH value of said first calibration fluid, and wherein the step of producing said predetermined, second calibration fluid comprises producing a second calibration fluid from said first calibration fluid having a pH value precisely determined from said pH value of said first calibration fluid.

9. A method as claimed in claim 8 wherein the step of providing said predetermined, first calibration fluid comprises providing a predetermined, first calibration fluid having a logarithm of the concentration of said gas in said first calibration fluid which is a non-constant linear function of said variable pH value of said first calibration fluid.

10. A method as claimed in claim 9 wherein the step of calibrating said sensor comprises:

produce, using said sensor to be calibrated, measured values comprising a concentration $U_{pG}(C)$ of said gas in said first calibration fluid and a concentration $U_{pG}(C')$ of said gas in said second calibration fluid;

supplying said first and second calibration fluids to a pH sensor and, using said pH sensor, producing a measured value $U_{pH}(C)$ proportional to the pH value of said first calibration fluid and a measured value $U_{pH}(C')$ of said second calibration fluid; and generating a calibration quantity $$-K_{pG}=(U_{pG}(C)-U_{pG}(C'))/(U_{pH}(C)-U_{pH}(C')).$$

11. A method as claimed in claim 1 wherein said gas in each of said first and second calibration fluids comprises $CO_2$, and wherein sensor to be calibrated comprises a $CO_2$ sensor for measuring the respective partial pressures of $CO_2$ in said first and second calibration fluids as respective indicators for the respective concentrations of $CO_2$ in said first and second calibration fluids.

12. A method as claimed in claim 11 wherein said predetermined, first calibration fluid comprises a fluid having $HCO_3^-$ dissolved therein.

13. A method as claimed in claim 1 wherein said first and second calibration fluids comprise a physiological body fluid having said gas dissolved therein in respectively different concentrations, and wherein said sensor to be calibrated comprises a sensor for measuring the respective partial pressures of said gas in said physiological body fluid.

14. A method as claimed in claim 13 wherein said first and second calibration fluids comprise blood with $CO_2$ dissolved therein respectively in said first and second concentrations, and wherein said sensor to be calibrated comprises a sensor for measuring a partial pressure of $CO_2$ in blood.

15. A method for measuring a partial pressure of $CO_2$ dissolved in blood using a $CO_2$ sensor for measuring said $CO_2$ partial pressure and for generating a corresponding measured value proportional to a logarithm of the $CO_2$ partial pressure comprising the steps of:

providing a predetermined, first calibration fluid having $CO_2$ dissolved therein with a defined physiological, first partial pressure and having $HCO_3^-$ dissolved therein with a defined physiological concentration having a defined physiological, first pH value;

providing a gas phase containing the same gas as is dissolved in said first calibration fluid, said gas in said gas phase being at a partial pressure in said gas phase differing from said partial pressure of said gas in said first calibration fluid, so that a partial pressure difference for said gas exists between said gas phase and said first calibration fluid;

separating said gas phase from said first calibration fluid by a gas-permeable wall;

producing a second calibration fluid from said first calibration fluid by material transport between said first calibration fluid and said gas phase exclusively by causing a material transport between said first calibration fluid and said gas phase through said gas-permeable wall by virtue of said partial pressure difference, said second calibration fluid differing from said first calibration fluid only by having a physiological, second $CO_2$ partial pressure therein differing from said first $CO_2$ partial pressure and a physiological, second pH value differing from said first pH value;

supplying said first and second calibration fluids successively, in an arbitrary sequence, to a $CO_2$ sensor and to a pH sensor;

providing a base line fluid having $CO_2$ dissolved therein with a concentration corresponding to a partial pressure of less than 10 Torr and having a defined, third physiological pH value differing from said first pH value;

additionally supplying said pH sensor with said base line fluid; using said $CO_2$ sensor and said pH sensor, producing a measured value $U_{pCO2}(c)$ corresponding to the first $CO_2$ partial pressure in said first calibration fluid, a measured value $U_{pCO2}(C')$ corresponding to the second $CO_2$ partial pressure of said second calibration fluid, a measured value $U_{pH}(C)$ corresponding to the first pH value of said first calibration fluid, a measured value $U_{pH}(C')$ corresponding to the second pH value of said second calibration fluid, and a measured value $U_{pH}(BF)$ corresponding to the third pH value of said base line fluid, and a measured value $U_{pCO2}(BF)$ corresponding to a $CO_2$ partial pressure of said base line fluid;

generating a quantity $$S_{pCO2}=K_{pCO2}\cdot S_{pH}$$

wherein $K_{pCO2}=-[(U_{pCO2}(C)-U_{pCO2}(C'))/(U_{pH}(C)-U_{pH}(C'))]$ and $S_{pH}=(\Delta U_{pH}(C)/(pH(C)-pH(BF))$ wherein $\Delta U_{pH}(C)=U_{pH}(C)-U_{pH}(BF)$;

supplying blood to said $CO_2$ sensor and obtaining a measured value $U_{pCO2}(B)$ corresponding to a $CO_2$ partial pressure of said blood;

calculating a logarithm of the $CO_2$ partial pressure of said blood $\log(pCO_2(B))$ according to $$\log(pCO_2(B))=(\Delta U_{pCO2}(B)-\Delta U_{pCO2}(C))/S_{pCO2}+\log(pCO2(C))$$

wherein $$\Delta U_{pCO2}(B) = U_{pCO2}(B) - U_{pCO2}(BF) \text{ and}$$

$$\Delta U_{pCO2}(C) = U_{pCO2}(C) - U_{pCO2}(BF); \text{ and}$$

identifying the $CO_2$ partial pressure in said blood from log(pCO2(B)).

16. A method as claimed in claim 15 wherein the $CO_2$ partial pressure of said base line fluid changes over time, and comprising the additional steps of:

forming the quantity $\Delta U_{pCO2}(C)$ by $$U_{pco2}(C) = U_{pco2}(C) - U_{pco2}(BF(t_c))$$

with a measured value $U_{pCO2}(BF(t_c))$ of the $CO_2$ partial pressure of the base line fluid measured close in time to the measurement of the first $CO_2$ partial pressure of the first calibration fluid at time $t_c$; and forming the quantity $\Delta U_{pCO2}(B)$ by $$\Delta U_{pco2}(B) = U_{pco2}(B) - U_{pco2}(BF(t_b))$$

using a measured value $U_{pCO2}(BF(t_b))$ of the $CO_2$ partial pressure of the base line fluid measured close in time to the measurement of the $CO_2$ partial pressure of said blood.

17. A method as claimed in claim 15 wherein the step of providing a predetermined, first calibration fluid comprises providing a predetermined, first calibration fluid having $NaHCO_3$ dissolved therein in a physiological concentration.

18. A method as claimed in claim 15 wherein the step of producing said second calibration fluid from said first calibration fluid comprises producing said second calibration fluid by allowing $CO_2$ to outgas from said first calibration fluid.

19. A method as claimed in claim 15 wherein the step of causing a material transport comprises:

supplying said first calibration fluid to said sensor through a tube having a gas-permeable tube wall comprising said gas-permeable wall, surrounded at an exterior by said gas phase and having an interior cross-section which is small relative to a quantity of said first calibration fluid to be delivered to said sensor per unit of time for preventing modification of said first concentration of said gas in said first calibration fluid beyond a prescribed amount due to said material transport during delivery of said first calibration fluid to said sensor; and producing said second calibration fluid from said first calibration fluid by allowing said first calibration fluid to temporarily dwell in said tube thereby producing a defined material transport between said first calibration fluid in said tube and said gas phase via said tube wall.

20. A method as claimed in claim 15 wherein the step of supplying a base line fluid comprises a base line fluid which is maintained air-saturated before delivery to said pH sensor.

21. A method as claimed in claim 20 wherein the step of supplying said base line fluid to said pH sensor comprises supplying said base line fluid to said pH sensor through a gas-permeable tube having an interior cross-section dimensioned large relative to a quantity of said base line fluid to be delivered to said pH sensor in a defined unit of time for causing said base line fluid to dwell in said tube during delivery to said pH sensor for a time for adapting said base line fluid to an ambient pressure.

22. A method as claimed in claim 21 wherein the step of supplying said base line fluid to said pH sensor comprises supplying said base line fluid from a gas-impermeable vessel to said pH sensor via said tube.

23. A method as claimed in claim 15 comprising the additional step of:

repeatedly using said quantity $S_{pCO2}$ for multiple identifications of $CO_2$ partial pressure of different blood samples by repeated, updated determination of the measured value $U_{pCO2}(B)$ and the measured value $U_{pCO2}(BF)$.

\* \* \* \* \*